US011013868B2

(12) United States Patent
Nakano

(10) Patent No.: US 11,013,868 B2
(45) Date of Patent: May 25, 2021

(54) FLAVOR INHALER

(71) Applicant: JAPAN TOBACCO INC., Tokyo (JP)

(72) Inventor: Takuma Nakano, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 233 days.

(21) Appl. No.: 15/718,211

(22) Filed: Sep. 28, 2017

(65) Prior Publication Data

US 2018/0014571 A1 Jan. 18, 2018

Related U.S. Application Data

(63) Continuation of application No. PCT/JP2015/060786, filed on Apr. 6, 2015.

(51) Int. Cl.
*A24F 47/00* (2020.01)
*A61M 11/04* (2006.01)
*A24D 1/22* (2020.01)
*A61M 15/06* (2006.01)
*A24D 1/00* (2020.01)

(52) U.S. Cl.
CPC .......... *A61M 11/047* (2014.02); *A24D 1/22* (2020.01); *A24D 1/002* (2013.01); *A61M 11/042* (2014.02); *A61M 15/06* (2013.01)

(58) Field of Classification Search
CPC .................................................. A24F 47/008
USPC ....................................................... 131/329
See application file for complete search history.

(56) References Cited

U.S. PATENT DOCUMENTS

| 2004/0226568 | A1 | 11/2004 | Takeuchi et al. |
| 2008/0047571 | A1 | 2/2008 | Braunshteyn et al. |
| 2008/0149118 | A1 | 6/2008 | Oglesby et al. |
| 2009/0065011 | A1* | 3/2009 | Maeder ................. A24F 47/006 131/194 |
| 2011/0180082 | A1* | 7/2011 | Banerjee ................ A24D 1/002 131/280 |
| 2014/0020698 | A1 | 1/2014 | Fiebelkorn |
| 2014/0334802 | A1 | 11/2014 | Dubief |
| 2015/0027454 | A1* | 1/2015 | Li ......................... A61M 11/044 131/328 |
| 2015/0027474 | A1 | 1/2015 | Zuber et al. |

(Continued)

FOREIGN PATENT DOCUMENTS

| CA | 2271432 A1 | 11/2000 |
| CN | 104203015 A | 12/2014 |

(Continued)

OTHER PUBLICATIONS

International Search Report, issued in PCT/JP2015/060786 (PCT/ISA/210), dated Jun. 23, 2015.

(Continued)

*Primary Examiner* — Eric Yaary

(74) *Attorney, Agent, or Firm* — Birch, Stewart, Kolasch & Birch, LLP

(57) ABSTRACT

A flavor inhaler comprises: a flavor source configured to generate flavor without combusting; a cylindrical holding member including at least the flavor source inside; a flow path that is provided in the cylindrical holding member and that is extending from the flavor source toward a suction port for sucking the flavor; and a cooling layer provided only downstream of the flavor source. The cooling layer is provided on an inner surface of the cylindrical holding member, and faces the flow path.

12 Claims, 4 Drawing Sheets

(56) References Cited

U.S. PATENT DOCUMENTS

| | | | |
|---|---|---|---|
| 2015/0053219 A1 | 2/2015 | Roudier et al. | |
| 2015/0245662 A1* | 9/2015 | Memari | A24F 15/12 131/328 |
| 2015/0313281 A1* | 11/2015 | Bonici | A24D 1/002 131/276 |
| 2016/0143356 A1* | 5/2016 | Poget | A24F 47/006 131/329 |
| 2016/0331032 A1* | 11/2016 | Malgat | A24F 42/10 |

FOREIGN PATENT DOCUMENTS

| | | |
|---|---|---|
| JP | 11-164679 A | 6/1999 |
| JP | 2015-504653 A | 2/2015 |
| JP | 2015-508676 A | 3/2015 |
| KR | 10-2000-0077188 A | 12/2000 |
| KR | 10-2004-0066928 A | 7/2004 |
| KR | 10-2009-0037908 A | 4/2009 |
| KR | 10-2014-0020293 A | 2/2014 |
| WO | WO 2013/120565 A2 | 8/2013 |
| WO | WO 2013/120849 A1 | 8/2013 |
| WO | WO-2014140273 A2 * | 9/2014 ........... A24F 47/004 |
| WO | WO 2015/022317 A1 | 2/2015 |
| WO | WO-2015022317 A1 * | 2/2015 ........... A24F 47/006 |

OTHER PUBLICATIONS

Extended European Search Report for European Application No. 15888428.8, dated Dec. 4, 2018.
Japanese Notification of Reasons for Refusal for corresponding Japanese Application No. 2017-510819, dated Dec. 26, 2017, including an English translation.
Taiwanese Office Action, dated Jan. 10, 2017, for Taiwanese Application No. 104143533, along with an English translation.
Korean Office Action, dated Jun. 25, 2020, for Korean Appiication No. 10-2019-7020011, with an English translation.
Korean Office Acton, dated Jun. 25, 2020, for Korean Application No. 10-2019-7020012; with an English translation.
Korean Office Action, dated Jun. 25, 2020, for Korean Appiication No. 10-2019-7020013, with an English translation.

* cited by examiner

FLAVOR INHALER

CROSS REFERENCE TO RELATED APPLICATIONS

This application is a Continuation of PCT International Application No. PCT/JP2015/060786, filed on Apr. 6, 2015, the entire contents of which are hereby expressly incorporated by reference into the present application.

TECHNICAL FIELD

The present invention relates to a flavor inhaler including a flavor source that generates flavor without combusting.

BACKGROUND ART

A flavor inhaler (smoking article), by which flavor is enjoyed without combusting a flavor source such as tobacco, has been proposed instead of a cigarette. Patent Literature 1 discloses a flavor inhaler including an aerosol generation source that generates aerosol without combusting. The flavor inhaler has a cooling element that cools the aerosol generated at the aerosol generation source.

CITATION LIST

Patent Literature

Patent Literature 1: WO 2013/120565

SUMMARY

A first feature is summarized as a flavor inhaler comprising: a flavor source configured to generate flavor without combusting; a cylindrical holding member including at least the flavor source inside; a flow path that is provided in the cylindrical holding member and that is extending from the flavor source toward a suction port for sucking the flavor; and a cooling layer provided only downstream of the flavor source, wherein the cooling layer is provided on an inner surface of the cylindrical holding member, and faces the flow path. The cooling layer preferably surrounds a second flow path, in at least a part of section of the second flow path.

A second feature is summarized as the flavor inhaler according to the first feature, wherein the cylindrical holding member has a hole to directly flow external air into the flow path, and at least a part of the cooling layer is provided downstream of the hole. Here, "directly flow" means that external air flows into the flow path without passing a flavor source.

A third feature is summarized as the flavor inhaler according to the second feature, wherein the hole is formed to flow external air into the flow path toward a direction crossing to a direction in which the flow path extends.

A fourth feature is summarized as the flavor inhaler according to the second feature or third feature, wherein the hole is provided on an opposite side to the suction port with respect to a center of the cylindrical holding member in the direction in which the flow path extends.

A fifth feature is summarized as the flavor inhaler according to any one of the second feature to the fourth feature, wherein a plurality of the holes are provided in a circumferential direction of the cylindrical holding member at intervals.

A sixth feature is summarized as the flavor inhaler according to the fifth feature, wherein one of the holes is arranged at a position displaced from a straight line connecting another one of the plurality of holes and a center axis of the cylindrical holding member.

A seventh feature is summarized as the flavor inhaler according to the first feature to the sixth feature, further comprising a first thermal conductor that transmits heat generated by a combustion heat source to the flavor source, the combustion heat source provided at an ignition end of the cylindrical holding member, wherein the cooling layer is separated from the first thermal conductor.

An eighth feature is summarized as the flavor inhaler according to the seventh feature, wherein the cylindrical holding member has a hole to directly flow external air into the flow path, and the hole is provided between the first thermal conductor and the cooling layer.

A ninth feature is summarized as the flavor inhaler according to the seventh feature or the eighth feature, wherein the cooling layer is formed by a same material as a material configuring the first thermal conductor.

A tenth feature is summarized as the flavor inhaler according to any one of the first feature to the ninth feature, wherein the cooling layer defines a single channel to pass the flavor.

An eleventh feature is summarized as the flavor inhaler according to any one of the first feature to the tenth feature, wherein inside of the cooling layer is hollow. Here, "hollow" means that any member is not present inside the cooling layer, other than a filter provided to the suction port.

An twelfth feature is summarized as the flavor inhaler according to any one of the first feature to the eleventh feature, wherein the cooling layer has a length equal to or longer than a half length of the flow path in the direction in which the flow path extends.

DESCRIPTION OF EMBODIMENTS

Figure 1:
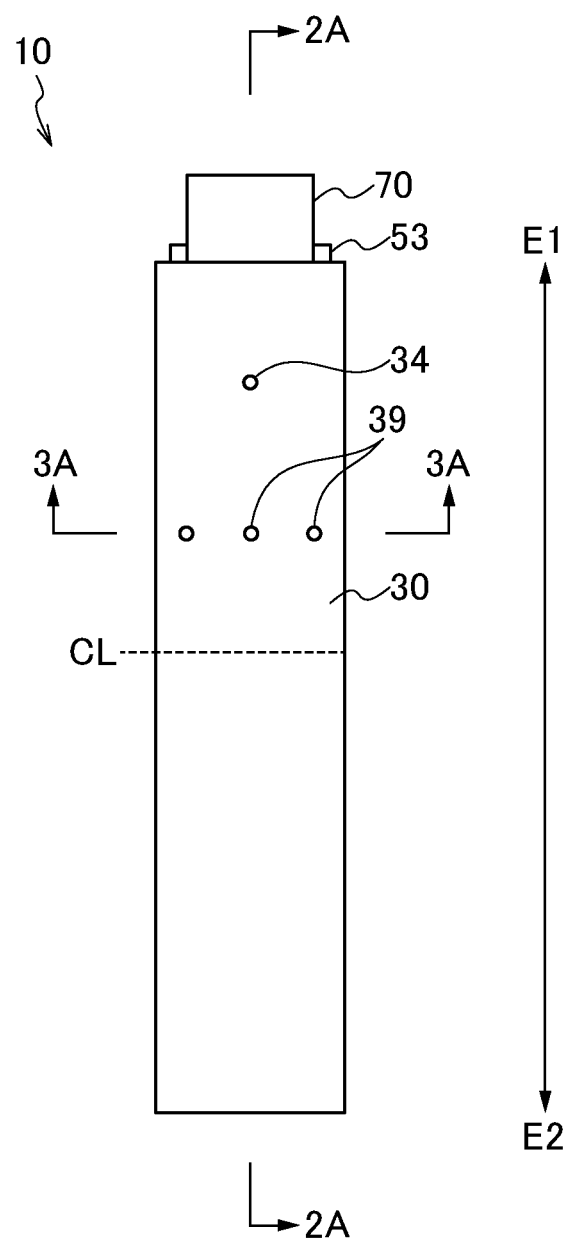
FIG. 1 is a side view of a flavor inhaler according to a first embodiment.

Embodiments are described below. In the description of the drawings below, same or similar reference numerals are given to same or similar parts. It should be noted that, however, the drawings are schematic, in which a ratio or the like of each dimension may differ from that in actuality.

Therefore, a specific dimension or the like should be determined in consideration of the following description. Naturally, even between the drawings, there is included a part in which a relation or a ratio of dimensions of those may differ from each other.

SUMMARY OF EMBODIMENTS

A flavor inhaler according to an embodiment includes: a flavor source that generates flavor without combusting; a cylindrical holding member including at least the flavor source inside; a flow path that is provided in the cylindrical holding member and extending from the flavor source toward a suction port where the flavor is sucked; and a cooling layer provided only downstream of the flavor source. In the flavor inhaler, the cooling layer is provided on an inner surface of the cylindrical holding member, and facing the flow path. Since the cooling layer facing the flow path is provided on the inner surface of the cylindrical holding member, inside of the cylindrical holding member does not need to be filled with a cooling element. For example, it is not necessary to fill inside of the holding member with a cooling element that is curled so as to form many channels, as described in Patent Literature 1. If inside of the cylindrical holding member is filled the cooling element, a ventilation resistance is increased, complicating a design of the ventilation resistance. In this embodiment, inside of the cylindrical holding member does not need to be filled with the cooling element, achieving an easy design of the ventilation resistance.

First Embodiment

Flavor Inhaler

Figure 2:
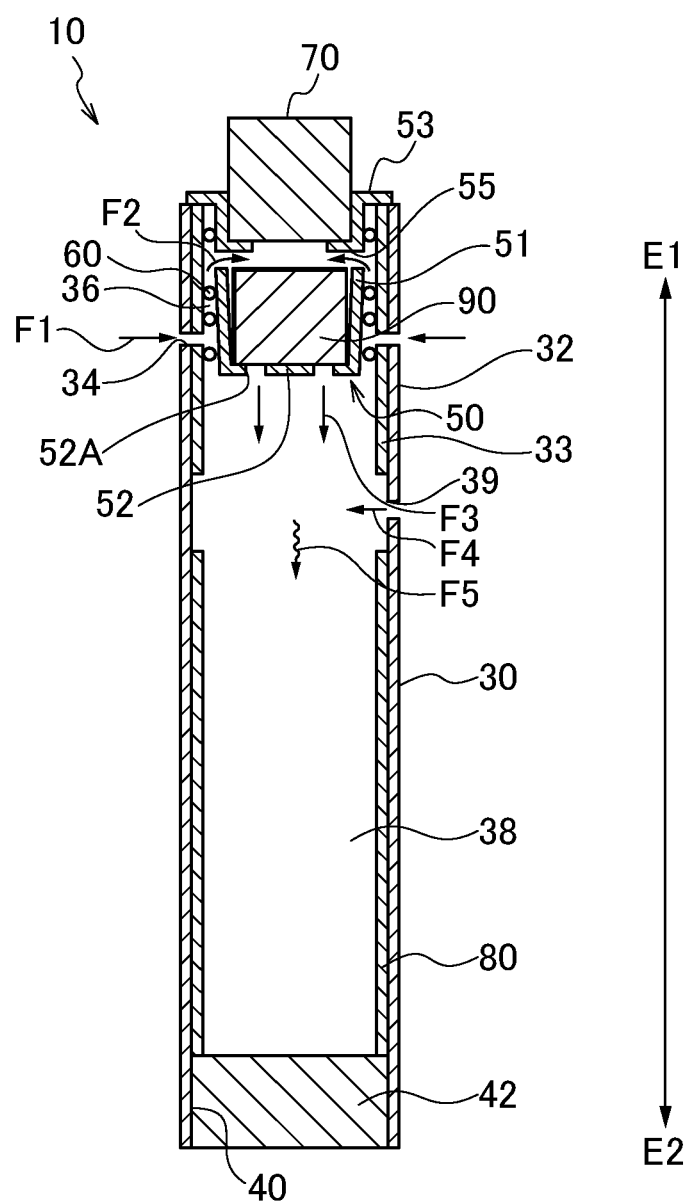
FIG. 2 is a cross-sectional view of the flavor inhaler along 2A-2A line in FIG. 1.
Figure 3:
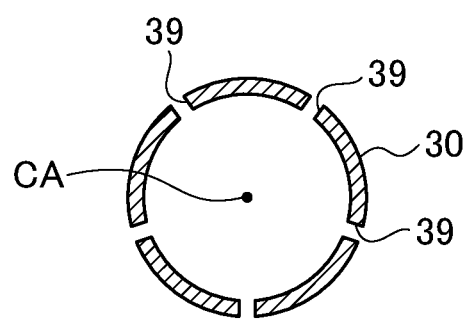
FIG. 3 is a cross-sectional view of the flavor inhaler along 3A-3A line in FIG. 1.

A flavor inhaler according to a first embodiment is described below. FIG. 1 is a side view of the flavor inhaler 10 according to the first embodiment. FIG. 2 is a cross-sectional view of the flavor inhaler 10 along 2A-2A line in FIG. 1. FIG. 3 is a cross-sectional view of the flavor inhaler 10 along 3A-3A line in FIG. 1. The flavor inhaler 10 has a cylindrical holding member 30, an inside holding member 50, a combustion heat source 70, and a flavor source 90.

The cylindrical holding member 30 extends from an ignition end E1 toward a non-ignition end E2. The ignition end E1 is an end on a side provided with the combustion heat source 70. Non-ignition end E2 is an end on a side provided with a suction port 40. The suction port 40 is positioned where a user holds in the mouth for sucking a flavor. The cylindrical holding member 30 may have, for example, a cylindrical shape or a rectangular cylindrical shape. An opening on the ignition end E1 side of the cylindrical holding member 30 is preferably closed. In this embodiment, at least the inside holding member 50 and the combustion heat source 70 close the opening on the ignition end E1 side of the cylindrical holding member 30. Thus, the flavor inhaler 10 is preferably configured such that gas does not enter into the cylindrical holding member 30 from the opening on the ignition end E1 side of the cylindrical holding member 30.

The inside holding member 50 is provided in the cylindrical holding member 30. However, a part of the inside holding member 50 may extend outside of the cylindrical holding member 30. The inside holding member 50 retains at least a part of the combustion heat source 70 and at least a part of the flavor source 90. The inside holding member 50 has the first side wall 51 in a cylindrical shape and an introduction port 55. The first side wall 51 surrounds at least a part of the flavor source 90 and at least a part of the combustion heat source 70. Alternatively, the first side wall 51 may surround at least a part of the flavor source 90 without surrounding the combustion heat source 70. The introduction port 55 is provided so as to introduce air to the flavor source 90 in the first side wall 51. The introduction port 55 may be formed from a hole formed on the first side wall 51.

The combustion heat source 70 is provided on the ignition end E1 side of the cylindrical holding member 30. The combustion heat source 70 is composed from a combustible material. The combustible material is, for example, a mixture including a carbon material, an incombustible additive, a binder (an organic binder or an inorganic binder), and water. As the carbon material, it is preferable to use a material from which volatile impurities have been removed by a heat treatment or the like. When a total weight of the combustion heat source 70 is 100 wt. %, the combustion heat source 70 preferably includes a carbonaceous material in a range of 30 wt. % to 70 wt. %, more preferably includes the carbonaceous material in a range of 35 wt. % to 45 wt. %.

The combustion heat source 70 is designed such that a part on the ignition end E1 side is burned, but an end part on a non-ignition end E2 side is not burned. Namely, the end part on the non-ignition end E2 side of the combustion heat source 70 forms a non-combustion part, while other part of the combustion heat source 70 forms a combustion part.

The flavor source 90 is provided inside the cylindrical holding member 30, on the non-ignition end E2 side from the combustion heat source 70. The flavor source 90 may be adjacent to the combustion heat source 70. The flavor source 90 is configured to generate flavor without combusting. To be more precise, the flavor source 90 generates flavor by heating with the combustion heat source 70.

As the flavor source 90, for example, a tobacco material can be used. In such a case, the flavor source 90 may include general cut tobacco that is used for cigarettes (paper rolled tobacco), and may include granular tobacco that is used for snuff tobacco. The flavor source 90 may include glycerin and/or propylene glycol, in addition to the tobacco material. The flavor source 90 may include a flavoring agent.

The cylindrical holding member 30 has a second side wall 32 having a cylindrical shape to surround the first side wall 51 of the inside holding member 50. The second side wall 32 may extend long from the ignition end E1 side toward the non-ignition end E2 side. The second side wall 32 may include, for example, a paper tube formed by deforming a rectangular cardboard into a cylindrical shape.

At least the first side wall 51 of the inside holding member 50 may be formed by a thermal conductor. Additionally, it is preferable that the inside holding member 50 is integrally formed by the thermal conductor. Heat conductivity of this thermal conductor at normal temperature is preferably equal to or more than 10 W/(m·K) in a direction along the ignition end E1 to the non-ignition end E2. As the thermal conductor, for example, stainless steel can be used. As the stainless steel, for example, SUS430 may be used. When the inside holding member 50 is made from stainless steel, a thickness of the first side wall 51 of the inside holding member 50 is preferably 0.1 mm or less.

The second side wall 32 of the cylindrical holding member 30 may include a first thermal conductor 33 facing the inside holding member 50. The first thermal conductor 33 is arranged so as to cover at least a part of at least the first side wall 51 of the inside holding member 50. The first thermal conductor 33 does not need to be directly in contact with the combustion heat source 70.

The first thermal conductor 33 promotes the heat conduction from the combustion heat source 70 to the flavor source 90. The first thermal conductor 33 preferably extends to the non-ignition end E2 side from an end face on the non-ignition end E2 side of the inside holding member 50. The first thermal conductor 33 is preferably formed from a metal material excellent in heat conductivity. Heat conductivity of the first thermal conductor 33 is preferably higher than heat conductivity of the first side wall 51. For example, the first thermal conductor 33 is formed from aluminum.

The second side wall 32 of the cylindrical holding member 30 has a through-hole 34 that is fluidly coupled to external air. The through-hole 34 may be provided on the ignition end E1 side from an end part on the non-ignition end E2 side of the flavor source 90.

At least between the first side wall 51 and the second side wall 32, a flow-path forming member 60 is provided. The flow-path forming member 60 defines a first flow path 36 inside the cylindrical holding member 30, for allowing external air to flow to the flavor source 90. The flow-path forming member 60 may also be formed from a member that is separate from the first side wall 51 and the second side wall 32. Alternatively, the flow-path forming member 60 may also be formed from a member that is integrally formed on the first side wall 51 or the second side wall 32. The first flow path 36 connects the through-hole 34 of the second side wall 32 and the introduction port 55 of the inside holding member 50, and passes between the first side wall 51 and the second side wall 32.

The inside holding member 50 may also have a thermal conductor (not shown) provided on an outer surface of the first side wall 51. This thermal conductor may be arranged so as to cover at least a part of at least the first side wall 51 of the inside holding member 50, as with the first thermal conductor 33. This thermal conductor promotes heat conduction from the combustion heat source 70 to the flavor source 90. This thermal conductor is preferably formed from a metal material excellent in heat conductivity, for example, formed from aluminum. When the inside holding member 50 has a thermal conductor adjacent to the outer surface of the first side wall 51, the first thermal conductor 33 does not need to be provided. In this case, the flow-path forming member 60 may be provided between the second side wall 32 and the thermal conductor on the outer surface of the first side wall 51.

In the cylindrical holding member 30, there is provided a second flow path 38 for allowing flavor generated at the flavor source 90 to flow to the suction port 40. The second flow path 38 connects the flavor source 90 and the suction port 40 where the flavor generated at the flavor source 90 is sucked. The introduction port 55 of the inside holding member 50 may be provided on the ignition end E1 side from the through-hole 34 of the cylindrical holding member 30. Additionally, the first flow path 36 is preferably provided only on the ignition end E1 side from the end part on the non-ignition end E2 side of the flavor source 90.

During a puff action of a user, external air enters into the first flow path 36 from the through-hole 34 (arrow F1 in FIG. 2). Then, the external air reaches the flavor source 90 through the introduction port 55 (arrow F2 in FIG. 2). The external air passing through the first flow path 36 reaches the flavor source 90 without coming into contact with the combustion part of the combustion heat source 70. The air having reached the flavor source 90 goes to the suction port 40 by passing through the second flow path 38, along with the flavor (arrows F3 and F5 in FIG. 2). Since the flavor source 90 is heated by the combustion heat source 70, a temperature of the gas passing the flavor source 90 to flow into the second flow path 38 is high.

The cylindrical holding member 30 has a hole 39 (hereinafter referred to as a "ventilation hole") that allows external air to directly flow into the second flow path 38. Here, "directly flow" means that external air flows into the second flow path 38 without passing the flavor source 90.

The ventilation hole 39 may be formed such that gas flows in a crossing direction to an extending direction of the second flow path 38 (arrow F4 in FIG. 2). For example, the ventilation hole 39 may be formed such that gas flows in toward a center axis of the second flow path 38, along a direction substantially orthogonal to the extending direction of the second flow path 38. It is preferable that a plurality of the ventilation holes 39 are provided on a circumferential direction of the cylindrical holding member 30 at intervals. In this case, the intervals between the ventilation holes 39 may be constant. The ventilation hole 39 may be provided on an opposite side to the suction port 40, with respect to a center CL of the cylindrical holding member 30 in the extending direction of the second flow path 38. The ventilation hole 39 is preferably provided between the first thermal conductor 33 and a cooling layer 80.

Any one of the plurality of ventilation holes 39 is preferably arranged at a position not opposed to another one among the plurality of ventilation holes 39, and is more preferably arranged at a position displaced from a straight line connecting another one among the plurality of ventilation holes 39 and a center axis CA of the cylindrical holding member 30 (see FIG. 3). In this case, each of the ventilation holes 39 is not arranged on an opposite side to each of the ventilation holes 39 across the center axis CA of the cylindrical holding member 30. Additionally, the plurality of ventilation holes 39 are preferably arranged at same positions to each other in a direction along the center axis CA of the cylindrical holding member 30. However, the plurality of ventilation holes 39 may also be arranged to be displaced to each other in a direction along the center axis CA of the cylindrical holding member 30.

The cooling layer 80 is a layer that cools flavor generated at the flavor source 90. The cooling layer 80 is provided on an inner surface of the cylindrical holding member 30 to face the second flow path 38. The cooling layer 80 preferably surrounds the second flow path 38, in at least a part of section of the second flow path 38. The cooling layer 80 is preferably provided only downstream of the flavor source 90. The cooling layer 80 preferably has a thickness not to remarkably increase a fluid resistance of the second flow path 38. Depending on a diameter of the second flow path 38, the thickness of the cooling layer 80 is, for example, preferably 5 μm or more to 500 μm or less. Further, in a cross section vertical to the center axis CA of the cylindrical holding member 30, a ratio of a cross-sectional area of the cooling layer 80 with respect to a cross-sectional area inside an inner wall of the cylindrical holding member 30 is preferably 0.2% or more to 45% or less, more preferably 0.5% or more to 5% or less. For example, in the cross section vertical to the center axis CA of the cylindrical holding member 30, an outer diameter of the cylindrical holding member 30 may be 5 mm to 8 mm, the thickness of the cylindrical holding member 30 may be 0.15 mm to 0.5 mm, and the thickness of the cooling layer 80 may be 0.05 mm to 0.5 mm.

In the first embodiment, the cooling layer 80 is provided only downstream of the ventilation holes 39. In other words, the cooling layer 80 does not reach the upstream side from the ventilation holes 39. Alternatively, a part of the cooling layer 80 may reach the upstream side of the ventilation holes 39. Namely, only at least a part of the cooling layer 80 needs to be provided downstream of the ventilation holes 39.

The cooling layer 80 preferably has a length equal to or longer than a half length of the second flow path 38 in the extending direction of the second flow path 38. The cooling layer 80 is preferably separated from the first thermal conductor 33 that composes the cylindrical holding member 30.

The cooling layer 80 preferably defines a single channel to be passed with the flavor, in the cylindrical holding member 30. More preferably, inside of the cooling layer 80 is hollow. Here, "inside of the cooling layer 80 is hollow"

means that any member is not present inside the cooling layer 80, other than a filter 42 provided to the suction port 40. In this case, a volume of a cavity portion in the second flow path 38 can be larger. In this embodiment, the cooling layer 80 defines the single channel in the cylindrical holding member 30, and inside of the cooling layer 80 is hollow.

In the first embodiment, inside of the cooling layer 80 is hollow. Alternatively, inside the cooling layer 80 may be provided with any member to an extent not to significantly increase a flow-path resistance of the second flow path 38. For example, a cylindrical member may be provided along the center axis of the second flow path. This cylindrical member may also be provided with another cooling layer on its outer peripheral surface.

The cooling layer 80 may include a second thermal conductor. The second thermal conductor may be metal. As an example, the cooling layer 80 may be formed from a metal pipe. Alternatively, the cooling layer 80 may be formed from a metal-laminated paper including a paper, and a metal layer that is laminated to the paper. As the metal described above, for example, aluminum can be used. Further, instead of these, the cooling layer 80 may also be a layer including polylactic acid (PLA). Furthermore, the cooling layer 80 may be formed from a same material as that of the first thermal conductor 33 that composes the cylindrical holding member 30.

The cooling layer 80 may have a plurality of projections and depressions for increasing a surface area of the cooling layer 80. Such projections and depressions can be formed, for example, by crepe processing of a surface of the cooling layer 80. These projections and depressions allow an increase in a heat-exchange-surface area of the cooling layer 80, without making the cross-sectional area of the second flow path 38 too small.

Operation and Effect

According to one embodiment, a flavor inhaler 10 has a cooling layer 80 provided only downstream of a flavor source 90, and the cooling layer 80 is provided on an inner surface of the cylindrical holding member 30 and facing a second flow path 38. Since the cooling layer 80 facing the second flow path 38 is provided on the inner surface of the cylindrical holding member 30, inside of the cylindrical holding member 30 does not need to be filled with a cooling element. If inside of the cylindrical holding member 30 is filled the cooling element, a ventilation resistance is increased, complicating a design of the ventilation resistance. In this embodiment, inside of the cylindrical holding member 30 does not need to be filled with the cooling element, achieving an easy design of the ventilation resistance.

According to one embodiment, a cylindrical holding member 30 has a ventilation hole 39 that allows external air to flow into a second flow path 38, and at least a part of a cooling layer 80 is provided downstream of the ventilation hole 39. Gas having passed the flavor source 90 is cooled by external air flowing in from the ventilation hole 39, and is passed to the second flow path 38 to which the cooling layer 80 faces. This enables an increase in cooling efficiency of the gas flowing in the second flow path 38 passing through the flavor source 90.

According to one embodiment, a ventilation hole 39 is formed such that external air flows into a second flow path 38 in a crossing direction to an extending direction of the second flow path 38. It has been found that a cooling layer 80 and an inflow of external air from the ventilation hole 39 cause synergistic improvement of cooling effect. This may be because a gas flow flowing toward a non-ignition end E2 in the second flow path 38 (arrow F3 in FIG. 3) is disturbed by external air flowing in from the ventilation hole 39 (arrow F4 in FIG. 3) to cause a turbulent flow, allowing the gas flow having passed the flavor source to easily come into contact with the cooling layer 80.

According to one embodiment, a ventilation hole 39 is provided on an opposite side to a suction port 40, with respect to a center CL of a cylindrical holding member 30 in an extending direction of a second flow path 38. Longer length of the second flow path 38 on a downstream side of the ventilation hole 39 allows increased cooling effect of gas having passed the flavor source 90. Moreover, the ventilation hole 39 is relatively far away from the suction port 40, preventing possibility that a user closes the ventilation hole 39 with a finger during a puff action.

According to one embodiment, a plurality of ventilation holes 39 are provided on a circumferential direction of a cylindrical holding member 30 at intervals. This enables uniform cooling of gas in a second flow path 38 in a circumferential direction of the second flow path 38.

According to one embodiment, a cooling layer 80 is separated from a first thermal conductor 33. This can prevent a direct flow of heat generated at a combustion heat source 70, into the cooling layer 80. This results in enabling prevention of a reduction in cooling effect of the cooling layer 80. Moreover, the heat generated at the combustion heat source 70 is effectively transmitted to a flavor source 90.

According to one embodiment, a ventilation hole 39 is provided between a first thermal conductor 33 and a cooling layer 80. Namely, the ventilation hole 39 is provided where the first thermal conductor 33 or the cooling layer 80 is not present. This provides an advantage that the ventilation hole 39 can be easily formed to a cylindrical holding member 30.

According to one embodiment, a cooling layer 80 is formed from a same material as that of a first thermal conductor 33. This allows the first thermal conductor 33 and the cooling layer 80 to be formed in a same process, enabling easy production of a flavor inhaler 10.

According to one embodiment, a cooling layer 80 defines a single channel to be passed with flavor. According to another embodiment, inside of a cooling layer 80 is hollow. This allows a ventilation resistance to be maintained relatively low, compared with an aspect in which inside of a cylindrical holding member 30 is filled with a cooling element curled so as to form a plurality of channels.

According to one embodiment, a cooling layer 80 has a length equal to or longer than a half length of a second flow path 38 in an extending direction of the second flow path 38. Since the cooling layer 80 extends thus relatively long, cooling efficiency of gas in the second flow path 38 can be promoted.

Second Embodiment

Figure 4:
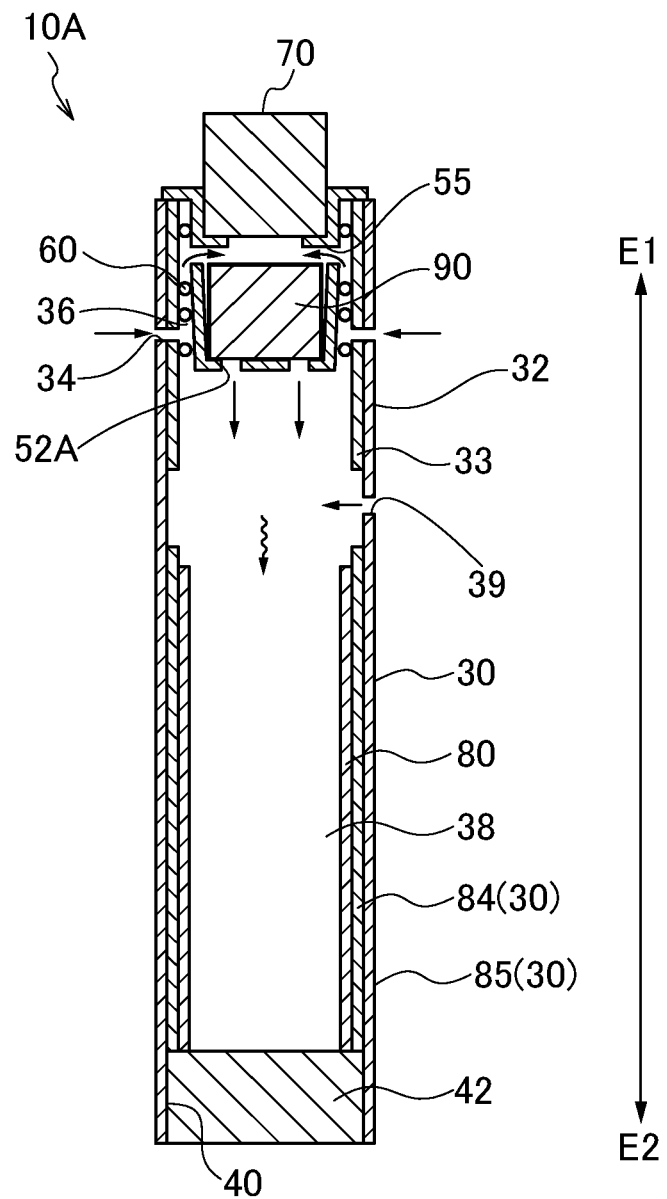
FIG. 4 is a cross-sectional view of a flavor inhaler according to a second embodiment.

A flavor inhaler 10A according to a second embodiment is described below with reference to FIG. 4. The same reference numerals are given to the same configurations as those of the first embodiment. Differences from the first embodiment are mainly described below.

In the second embodiment, a cylindrical holding member 30 has a plurality of layers, at least at a section provided with a second flow path 38. For example, the cylindrical holding member 30 may have an outer-wall portion 85, and an inner-wall portion 84 provided inside the outer-wall portion.

The inner-wall portion 84 may be formed from a sheet attached to an inner surface of the outer-wall portion 85. Alternatively, the inner-wall portion 84 may also be formed from a pipe member inserted into the outer-wall portion 85.

The cooling layer 80 is provided on an inner surface of the cylindrical holding member 30, namely, on an inner surface of the inner-wall portion 84. Thus, the cooling layer 80 may also be formed on the inner surface of the cylindrical holding member 30 that has a plurality of layers. In this case, from a viewpoint of a flow-path resistance, a thickness of the cylindrical holding member 30 and a thickness of the cooling layer 80 are preferably designed so as not to make a cross-sectional area of the second flow path 38 too small. The cross-sectional area of the second flow path 38 in a cross section vertical to a center axis CA of the cylindrical holding member 30 is preferably 5 mm$^2$ or more to 50 mm$^2$ or less, more preferably 15 mm$^2$ or more to 35 mm$^2$ or less. For example, in the cross section vertical to the center axis CA of the cylindrical holding member 30, an outer diameter of the cylindrical holding member 30 may be 5 mm to 8 mm, the thickness of the cylindrical holding member 30 may be 0.15 mm to 0.5 mm, and the thickness of the cooling layer 80 may be 0.05 mm to 0.5 mm.

Other Embodiments

Although the present invention has been described with the above-described embodiments, the descriptions and drawings forming a part of the disclosure should not be construed as limiting the present invention. From this disclosure, various alternative embodiments, examples, and operation techniques will be apparent to those skilled in the art.

For example, the features described in the above-described plural embodiments can be combined as much as possible.

INDUSTRIAL APPLICABILITY

According to an embodiment, a flavor inhaler including a cooling layer enabling an easy design of a ventilation resistance can be provided.

The invention claimed is:

1. A flavor inhaler comprising:
a flavor source configured to generate flavor without combusting;
an inside holding member including a first side wall surrounding at least a part of the flavor source and an introduction port provided so as to introduce air from an upstream end of the flavor source to the flavor source in the first side wall;
a cylindrical holding member including a second side wall surrounding the first side wall and having a through-hole that is fluidly coupled to external air;
a first flow path that connects the through-hole of the second side wall and the introduction port of the inside holding member, and passes between the first side wall and the second side wall;
a second flow path that is provided in the cylindrical holding member and that is extending from the flavor source toward a suction port for sucking the flavor; and
a cooling layer provided only downstream of the flavor source, wherein
the cooling layer is provided on an inner surface of the cylindrical holding member, and faces the second flow path, and wherein the through-hole of the second side wall and the introduction port of the inside holding member are axially distanced from each other with respect to a longitudinal axis of the flavor inhaler.

2. The flavor inhaler according to claim 1, wherein the cylindrical holding member has a hole to directly flow external air into the second flow path, and at least a part of the cooling layer is provided downstream of the hole.

3. The flavor inhaler according to claim 2, wherein the hole is formed to flow external air into the second flow path toward a direction crossing to a direction in which the second flow path extends.

4. The flavor inhaler according to claim 2, wherein the hole is provided on an opposite side to the suction port with respect to a center of the cylindrical holding member in the direction in which the second flow path extends.

5. The flavor inhaler according to claim 2, wherein a plurality of the holes are provided in a circumferential direction of the cylindrical holding member at intervals.

6. The flavor inhaler according to claim 5, wherein one of the holes is arranged at a position displaced from a straight line connecting another one of the plurality of holes and a center axis of the cylindrical holding member.

7. The flavor inhaler according to claim 1, further comprising a first thermal conductor that transmits heat generated by a combustion heat source to the flavor source, the combustion heat source provided at an ignition end of the cylindrical holding member, wherein
the cooling layer is separated from the first thermal conductor.

8. The flavor inhaler according to claim 7, wherein the cylindrical holding member has a hole to directly flow external air into the second flow path, and the hole is provided between the first thermal conductor and the cooling layer.

9. The flavor inhaler according to claim 7, wherein the cooling layer is formed by a same material as a material configuring the first thermal conductor.

10. The flavor inhaler according to claim 1, wherein the cooling layer defines a single channel to pass the flavor.

11. The flavor inhaler according to claim 1, wherein inside of the cooling layer is hollow.

12. The flavor inhaler according to claim 1, wherein the cooling layer has a length equal to or longer than a half length of the second flow path in the direction in which the second flow path extends.

* * * * *